United States Patent [19]

Lammerant et al.

[11] Patent Number: 4,579,955

[45] Date of Patent: Apr. 1, 1986

[54] AMINO ACID SALTS OF 3-HYDROXYBUTANOIC ACID

[75] Inventors: Jacques Lammerant, Namur; Jaroslaw Kolanowski, Wezembeek-Oppen, both of Belgium

[73] Assignee: Solvay & Cie (Société Anonyme), Brussels, Belgium

[21] Appl. No.: 468,385

[22] Filed: Feb. 22, 1983

[30] Foreign Application Priority Data

Feb. 23, 1982 [FR] France ................................ 82 03100

[51] Int. Cl.$^4$ .................. C07C 101/26; C07D 233/64
[52] U.S. Cl. .................... 548/344; 548/496; 260/501.11; 260/501.12; 260/501.17
[58] Field of Search ............................ 548/344, 496; 260/501.17, 501.11, 501.12

[56] References Cited

U.S. PATENT DOCUMENTS

| | | | |
|---|---|---|---|
| 2,101,097 | 12/1937 | Rider et al. | 424/311 |
| 2,799,684 | 7/1957 | Morris | 548/496 |
| 3,830,931 | 8/1974 | De Felice | 424/319 |
| 3,879,537 | 4/1975 | Van Scott et al. | 424/311 |
| 3,920,835 | 11/1975 | Van Scott et al. | 424/311 |

FOREIGN PATENT DOCUMENTS 3206350 9/1982 Fed. Rep. of Germany .

OTHER PUBLICATIONS

Chemical Abstracts, vol. 29, (1935), col. 5601.7.
Chemical Abstracts Registry Handbook, (1965-1971), p. 5751R, No. 16974-59-7.
Nowak et al., Chemical Abstracts, vol. 83, (1975), No. 108261p.
Webb et al., Chemical Abstracts, vol. 43 (1949), col. 9210g.
Hellman et al., Chemical Abstracts, vol. 72, (1970), No. 18825u.

*Primary Examiner*—Robert W. Ramsuer
*Attorney, Agent, or Firm*—Spencer & Frank

[57] ABSTRACT

Pharmaceutical compositions containing 3-hydroxybutanoic acid or a salt derived from this acid, such as a sodium salt or alternatively a salt derived from an organic nitrogen base such as an amine; the amine can be an aminoacid of natural origin, such as arginine.

The compositions and the compounds according to the invention can be used for the prophylactic and curative treatment of cardiomyopathy of non-ischaemic and ischaemic origin.

4 Claims, No Drawings

AMINO ACID SALTS OF 3-HYDROXYBUTANOIC ACID

The present invention relates to pharmaceutical compositions for the metabolic protection of the myocardium in cases of complaints such as cardiomyopathy of ischaemic or non-ischaemic origin. It also relates to compounds which can be used in these compositions, which are salts derived from 3-hydroxybutanoic acid.

The compositions according to the invention contain 3-hydroxybutanoic acid or a salt derived from this acid.

The compounds according to the invention are salts derived from 3-hydroxybutanoic acid and from an organic nitrogen base.

The salts present in the compositions according to the invention can be derived from any inorganic or organic base. They can be, in particular, ammonium salts or metal salts; in the latter case, they can be derived from metals of groups Ia, IIa and IIb of the periodic table of the elements, such as zinc, calcium and, more particularly, sodium.

The compounds according to the invention can be salts derived from 3-hydroxybutanoic acid and from any organic nitrogen base. Preferably, however, the organic nitrogen base is an amine. This can be, in particular, an amine of the formula $NH_2R$, in which R represents an aliphatic radical containing up to 15 carbon atoms. Usually, R is further substituted by other functional groups such as $NR_1R_2$ and $COOR_3$, in which $R_1$, $R_2$ and $R_3$ independently of one another represent hydrogen or an aliphatic group containing up to 6 carbon atoms. Preferably, R contains from 4 to 12 carbon atoms in its molecule. More particular preference is afforded to the salts derived from aminoacids and, amongst these, to the salts derived from aminoacids of natural origin and even more to the salts derived from aminoacids of natural origin and in the L isomeric form. Good results can be obtained with the salts derived from aminoacids of natural origin and in the L isomeric form which can contain at least two nitrogen groups per carboxyl group, and, more particularly, with the salts derived from L-lysine, L-histidine and L-arginine. The best results have been obtained with the salts derived from L-arginine. The compounds described above are preferred for the pharmaceutical compositions according to the invention.

The 3-hydroxybutanoic acid which is present in the compositions according to the invention and from which the salts present in the compositions according to the invention are derived, and also the compounds according to the invention, can be in various isomeric forms such as the L(+) and racemic forms. Preferably, however, this acid is in the D(−) isomeric form. The 3-hydroxybutanoic acid can be obtained by any known method of synthesis, such as direct chemical or biochemical syntheses. The D(−)-3-hydroxybutanoic acid can advantageously be obtained by the depolymerisation of natural polymers extracted from biomasses, by the process described in European Patent Application No. 0,043,620 (SOLVAY & Cie).

The salts of 3-hydroxybutanoic acid can be prepared by any suitable organic synthesis. As regards the salts derived from 3-hydroxybutanoic acid in the D(−) or L(+) isomeric form and from an amine, and more particularly from aminoacids of natural origin, the preferred process consists in reacting the 3-hydroxybutanoic acid with the aminoacid of natural origin in a suitable solvent, such as water, and at a temperature of between 20° C. and 80° C. and preferably of between 30° and 50° C.; to do this, the general method is to use media containing the 3-hydroxybutanoic acid and the aminoacid of natural origin in equimolar amounts or in amounts such that the 3-hydroxybutanoic acid is slightly in excess relative to stoichiometry, with vigorous stirring and at a pressure of the order of atmospheric pressure. The concentrations of the media used vary between 0.5 and 8 molar in respect of 3-hydroxybutanoic acid and of aminoacid; preferably, this concentration is between 1 and 6 molar. The end of the reaction is characterized by thickening or solidification of the reaction mixture. The salts can then be recovered by the usual methods, such as evaporation of the solvent, the salts being obtained in solid form; they can then be subjected, if appropriate, to one or more recrystallisations.

The compounds and compositions according to the invention can be used as medicaments and, in particular, for the treatment and prevention of metabolic complaints of the myocardium in human medicine and in veterinary medicine. In this case, they are preferably formulated for use as a pharmaceutical means intended for internal treatment. Furthermore, these compounds and compositions can also be used for treating or preventing other complaints, such as complaints resulting from deficiencies in the metabolism of ketone substances or epilepsy; in this case, it is preferred to work with compounds or compositions based on salts derived from 3-hydroxybutanoic acid and from zinc, and very particularly with the salts derived from the abovementioned aminoacids.

The compositions according to the invention can consist solely of 3-hydroxybutanoic acid or of salts derived therefrom, but usually contain formulation additives enabling them to be administered conveniently, for example in the form of powders, tablets, capsules, coated tablets, pills, granules, suppositories, gelatin capsules, ampoules, syrups, emulsions, solutions or suspensions. These additives can be carriers or non-toxic solvents normally used in pharmacy, such as water, organic solvents of the paraffinic type, and vegetable and aliphatic alcoholic oils, inorganic salts and usual fillers, emulsifying agents of the polyoxyalkylene type or of the aromatic or aliphatic sulphonate type, cellulose derivatives, starch, dispersants, lubricants such as stearic acid salts or talc, binders and customary sweeteners or flavourings.

The pharmaceutical compositions according to the invention generally contain between 1% and 99% by weight of one or more 3-hydroxybutanoic acids or salts derived from these acids. They can be administered for treating or preventing metabolic disorders of the myocardium in all mammals, but in particular in human patients, in the form of one or more "dosage units" or "administration doses" in a pharmaceutically effective amount.

The term "dosage unit" or "administration dose" is understood as meaning a unit dose which can be administered to a patient and can easily be handled and packaged, while remaining in the form of a physically stable unit dose containing the active ingredient either by itself or in a mixture with solid or liquid pharmaceutical diluents or carriers.

The compositions according to the invention can be formulated, in particular, for oral administration, rectal administration, administration by intramuscular injection or administration by intravenous perfusion.

If they are intended for oral administration in solid form, the compositions can contain up to 5 g of 3-hydroxybutanoic acid per administration dose. Usually, the doses contain between 0.1 g and 3 g, and preferably between 0.5 g and 2 g, of 3-hydroxybutanoic acid or an equivalent amount of salt.

The compositions according to the invention which are presented in liquid form and are intended for oral administration can be solutions, emulsions or suspensions, which may or may not be syrupy. The amount of 3-hydroxybutanoic acid, or of salt derived therefrom, which they usually contain is generally between 1 g and 750 g, and preferably between 10 and 500 g, per liter of liquid.

If they are intended for administration by intramuscular injection, the compositions according to the invention can be formulated, under sterile conditions, in a concentrated form or a form which is ready for use, so that they usually contain at least 0.05% by weight, and preferably between 0.1% and 30% by weight, of 3-hydroxybutanoic acid, the maximum concentration being fixed by the isotonicity with the blood serum. In the case of the sodium salt of D(−)-3-hydroxybutanoic acid, the preferred concentrations of the liquids ready for injection are between 1 g and 20 g per liter of liquid. In the case of the arginine salt of D(−)-3-hydroxybutanoic acid, the preferred concentrations of the liquids ready for injection are between 1 and 45 g per liter of liquid. In the case where hypotonic formulations are used, the isotonicity can be obtained by incorporating agents known for this purpose, such as sodium chloride or dextrose. The formulations can also contain sterile diluents such as water, non-volatile oils, polyethylene glycols, glycerol and polypropylene glycols, antibacterial agents such as benzyl alcohol, antioxidants such as ascorbic acid and sodium bisulphite, chelating agents, and buffers such as acetates, citrates or phosphates, which are physiologically compatible.

The formulations intended for administration by intramuscular injection can be packaged in any of the usual ways and can be presented, in particular, in glass or plastic ampoules or syringes to be discarded after use.

The compositions according to the invention which are intended for administration by intravenous perfusion can also be formulated using the techniques and additives normally used in this field. The concentrations of 3-hydroxybutanoic acid, or of salt derived therefrom, in formulations of this type are generally more than 0.001% by weight. In the case of the sodium salt of D(−)-3-hydroxybutanoic acid, the concentration normally used varies between 0.05 g and 20 g, and preferably between 0.1 and 15 g, f per liter of liquid. In the case of the D(−)-3-hydroxybutanoic acid salt derived from arginine, these concentrations usually vary between 0.05 and 45 g, and preferably between 0.1 and 35 g, per liter of liquid.

The pharmaceutical compositions according to the invention can contain other principles which are active against complaints of the cardiac system or of the blood circulation. Amongst these active principles, examples which may be mentioned are cardiotonic heterosides, glucocorticoids, beta-blockers, calcium antagonists, agents making it possible to lower the blood pressure, antiarrhythmics and anticoagulants, provided there is compatibility.

The pharmaceutical compositions according to the invention can be used for the metabolic protection of the myocardium in prophylactic or curative treatments, in particular in cases of intense physical activities, such as sporting activities or energetic occupations, imposing excess oxygen consumption on an ostensibly normal heart, in cardiomyopathy of non-ischaemic origin, in cardiomyopathy of ischaemic origin, such as angina pectoris or myocardial infarction, in myocardial ischaemia resulting from a collapse of the coronary perfusion pressure, such as observed in states of circulatory shock through haemorrhaging, and, in general, in any situation of adrenergic discharge, such as observed in states of stress or of severe traumatism.

The mode of action of the compositions according to the invention proves to be particularly novel. In fact, hitherto, it was usual to overcome the insufficiencies in provision of oxygen to the myocardium, due to myocardial ischaemia, by reducing the effort to be exerted. Now, experiments on dogs, carried out with the compositions according to the invention, have shown that the mechanical efficiency indices of the heart, such as the ratio of the mean aortic pressure to the myocardial oxygen consumption, are improved. The doses to be administered daily can vary within wide limits, but are generally calculated so as to represent 0.001 and 1 g of 3-hydroxybutanoic acid, or of salt derived therefrom, per kg of weight; the preferred daily dose is between 0.005 and 0.5 g/kg.

The invention is illustrated by the examples which follow.

EXAMPLE 1

Preparation of the L(+)-arginine salt of D(−)-3-hydroxybutanoic acid 1 kg of an aqueous solution containing 593 g (5.7 mols) of D(−)-3-hydroxybutanoic acid is introduced into a cylindrical reactor which is equipped with a jacket making it possible to cool or heat the reactor, has a height of 30 cm and a diameter of 11 cm and is equipped with a stirrer having 4 blades covered with polyvinylidene fluoride. The whole is stirred violently and 960 g of L(+)-arginine are introduced in the course of 5 minutes. When the temperature of the reaction mixture reaches 45° C., the mixture is cooled by circulating water at 20° C. through the jacket, while at the same time continuing to stir the mixture. A gradual thickening of the suspension is observed, and the mixture finally solidifies 15 minutes after the introduction of the L(+)-arginine has ended. The solid is then recovered and dried to constant weight in a vacuum oven at 50° C. Finally, an L(+)-arginine salt of D(−)-3-hydroxybutanoic acid is recovered which has a melting point of between 100° and 105° C. and an optical rotation $[\alpha]_D^{27°\ C.}$ of 2.32°, measured on an aqueous solution having a concentration of 4.60 g/100 mL, at 27° C.

EXAMPLE 2

Experiment 1

This experiment is carried out by way of comparison on six dogs, identified as A, B, C, D, E and F, whose sex and weight are given in Table I below, which are anaesthetised by the subcutaneous injection of 2 mg/kg of morphine and the administration of 30 mg/kg of nembutal, and which are kept under artificial respiration by means of a Starling pump. The aortic pressure, the myocardial oxygen consumption, the oxygen partial pressure in the coronary venous blood, the coronary flow and the aortic pH are measured, together with the myocardial consumption of lactate, glucose, free fatty acids and 3-hydroxybutanonate. The average values observed are given in Table III below.

TABLE I

| Dog | Sex | Weight in Kg |
|---|---|---|
| A | M | 24.5 |
| B | M | 29 |
| C | M | 38 |
| D | F | 25 |
| E | F | 24 |
| F | M | 26.5 |

EXPERIMENT 2

This experiment is also carried out by way of comparison.

The six dogs of Experiment 1, kept under the above-mentioned conditions of anaesthesia, are subjected to adrenergic stimulation by the intravenous infusion of noradrenaline at the doses and for the periods given in Table II below.

TABLE II

| Dog | Amount of noradrenalin in ng/kg.minute | Period in minutes |
|---|---|---|
| A | 400 | 15 |
| B | 1,000 | 15 |
| C | 400 | 20 |
| D | 400 | 10 |
|   | 800 | 10 |
| E | 400 | 10 |
|   | 800 | 10 |
|   | 1,600 | 10 |
| F | 1,000 | 15 |

The same parameters are measured as in Experiment 1, and the average values of these measurements are given in Table III below.

Experiment 3

This experiment is carried out using a composition according to the invention.

Experiment 2 is repeated on the same dogs, except that the animals receive an intravenous infusion of the sodium salt of D(—)-3-hydroxybutanoic acid at a rate of 80 micromols per kg of body weight and per minute.

The average values of the parameters measured are given in Table III below.

TABLE III

| Parameter | Experiment | | |
|---|---|---|---|
|  | 1 | 2 | 3 |
| Aortic pressure in mm Hg | 106 | 122 | 136 |
| Myocardial oxygen consumption in ml/100 g. minute | 8.1 | 13.8 | 12.5 |
| Oxygen partial pressure in the coronary venous blood in mm Hg | 22.9 | 24.4 | 24.4 |
| Coronary flow in ml/100 g. minute | 82 | 120 | 131 |
| Aortic pH | 7.401 | 7.338 | 7.392 |
| Concentration of 3-hydroxy-butanoate in the arterial plasma in millimol °/₀₀ | 0.02 | 0.13 | 5.97 |
| Myocardial consumption of - | | | |
| Lactate in μmols/ 100 g. minute | 18 | 0 | 0 |
| glucose in μmols/ 100 g. minute | 8 | 0 | 0 |
| free fatty acids in μmols/ 100 g. minute | 6 | 16 | 10 |
| 3-hydroxybutanoate in μmols/100 g. minute | 0.2 | 2.3 | 73 |

A comparison of the results in Table III shows that the administration of the sodium salt of D(—)-3-hydroxybutanoic acid causes a reduction in the actual oxygen consumption of the myocardium subjected to an adrenergic discharge (comparison of Experiments 2 and 3) and an increase in the ratio of the aortic pressure to the oxygen consumption, which becomes higher (comparison of Experiments 2 and 3) and approaches the values measured at rest (comparison of Experiments 1 and 3).

The results also show that the assimilation of the free fatty acids drops in favour of the 3-hydroxybutanoate (comparison of Experiments 2 and 3) and approaches the values observed with the unstimulated myocardium (comparison of Experiments 1 and 3).

Finally, the metabolic acidosis triggered by the adrenergic discharge is corrected (comparison of Experiments 1, 2 and 3).

EXAMPLE 3

Experiments 4 to 6

The experiments described above are repeated on a male dog weighing 28 kg, but with stimulation effected by means of the intravenous infusion of 200 ng/kg.minute of noradrenalin for 25 minutes and the intravenous administration of 40 micromols/kg.minute of the L-arginine salt of the D(—)-3-hydroxybutanoic acid of Example 1. The parameters measured in the course of the experiment (Experiment 6) and in the course of comparison experiments carried out in the absence of stimulation and of treatment (Experiment 4), and by effecting the stimulation but not the treatment (Experiment 5), are given in Table IV below.

TABLE IV

| Parameter | Experiment | | |
|---|---|---|---|
|  | 4 | 5 | 6 |
| Aortic pressure in mm Hg | 94 | 132 | 94 |
| Myocardial oxygen consumption in ml/100 g. minute | 8.9 | 13.4 | 6.9 |
| Oxygen partial pressure in the coronary venous blood in mm Hg | 15.3 | 17.8 | 14.7 |
| Coronary flow in ml/100 g. minute | 70 | 104 | 56 |
| Aortic pH | 7.390 | 7.355 | 7.391 |
| Concentration of 3-hydroxy-butanoate in the arterial plasma in millimol °/₀₀ | 0.02 | 0.02 | 1.95 |
| Myocardial consumption of - | | | |
| Lactate in μmols/ 100 g. minute | 28.6 | 37.0 | 19.8 |
| glucose in μmols/ 100 g. minute | 22.4 | 21.7 | 4.6 |
| free fatty acids in μmols/100 g. minute | 2.4 | 10.7 | 1.8 |
| 3-hydroxybutanoate in μmols/100 g. minute | 0.2 | 0.3 | 24.1 |

A comparison of the results in Table IV shows that the administration of the arginine salt of D(—)-3-hydroxybutanoic acid (Experiment 6) makes it possible to reduce the actual oxygen consumption of the myocardium subjected to adrenergic stimulations below the values measured with and without adrenergic stimulation (comparison of Experiments 4 and 5), and also to increase the ratio of the aortic pressure to the oxygen consumption.

The results also show that the assimilation of the free fatty acids is normalised and that the blood pH is kept at normal values (Experiments 4, 5 and 6).

Moreover, a comparison of the values in Tables III and IV (Experiments 3 and 6) shows that the salts derived from arginine have the advantage over the sodium salts of stabilising the aortic pressure at values identical to those measured in the absence of adrenergic stimulation (Experiments 1 and 4).

EXAMPLE 4

Experiments 7 to 9

The experiments described in Example 2 are repeated, but they are carried out with 10 dogs having an average body weight of about 29 kg and with stimulation effected by means of an average infusion in the left ventricular cavity of 500 ng/kg.minute of noradrenalin for 20 minutes and the intravenous administration of 80 micromols/kg.minute of the L-arginine salt of D(—)-3-hydroxybutanoic acid of Example 1. The average of the ten values measured in the course of the experiment (Experiment 9) and in the course of comparison experiments carried out in the absence of stimulation and of treatment (Experiment 7), and by effecting the stimulation but not the treatment (Experiment 8), are given in Table V below.

TABLE V

| Parameter | Experiment (average of 10 values) | | |
|---|---|---|---|
| | 7 | 8 | 9 |
| Aortic pressure in mm Hg | 124 | 141 | 136 |
| Myocardial oxygen consumption in ml/100 g. minute | 8.5 | 12.3 | 8.9 |
| Oxygen partial pressure in the coronary venous blood in mm Hg | 20.3 | 21.4 | 21.0 |
| Coronary flow in ml/100 g. minute | 79 | 96 | 79 |
| Aortic pH | 7.396 | 7.333 | 7.344 |
| Concentration of 3-hydroxybutanoate in the arterial plasma in millimol °/$_{oo}$ | 0.04 | 0.11 | 8.30 |
| Myocardial consumption of - | | | |
| lactate in μmols/100 g. minute | 12.0 | 4.9 | 2.2 |
| glucose in μmols/100 g. minute | 14.4 | 4.7 | 2.8 |
| free fatty acids in μmols/100 g. minute | 4.4 | 16.9 | 5.5 |
| 3-hydroxybutanoate in μmols/100 g. minute | 0.7 | 1.8 | 35.8 |

A comparison of the results in Table V shows that the administration of the arginine salt of D(—)-3-hydroxybutanoic acid (Experiment 9) makes it possible to reduce the actual oxygen consumption of the myocardium subjected to adrenergic stimulations, relative to the values measured with adrenergic stimulation but without administration of the salt of D(—)-3-hydroxybutanoic acid (comparison with Experiment 8).

EXAMPLE 5

Preparation of pharmaceutical compositions

| Experiment 1: As tablets | |
|---|---|
| Sodium salt of D(—)-3-hydroxybutanoic acid | 500 mg |
| Lactose | 170 mg |
| Starch powder | 110 mg |
| Colloidal silicic acid | 10 mg |
| Magnesium stearate | 10 mg |
| | 800 mg |

The preparation is carried out by mixing the sodium salt of D(—)-3-hydroxybutanoic acid with some of the adjuvants and converting the mixture to granules in the presence of an aqueous starch solution. After the granules have been dried, the remainder of the adjuvants are added and the mixture is compressed to form tablets.

| Experiment 2 : As a solution for oral administration | |
|---|---|
| Arginine salt of D(—)-3-hydroxybutanoic acid | 20 g |
| Essence of peppermint | 0.4 g |
| Saccharin | 0.1 g |
| Distilled water | 400 g |
| | 420.5 g |

The arginine salt of D(—)-3-hydroxybutanoic acid is mixed with the essence of peppermint and the saccharin, the whole is dissolved in the water and the solution is introduced into 500 cm³ bottles.

| Experiment 3 : Ampoules for injections | |
|---|---|
| Sodium salt of D(—)-3-hydroxybutanoic acid | 20 mg |
| Double distilled water | 2 g |
| | 2.2 g |

The sodium salt is dissolved in the double distilled water and this solution is introduced into the ampoules under sterile conditions.

| Experiment 4 : Solution for intravenous perfusion | |
|---|---|
| Arginine salt of D(—)-3-hydroxybutanoic acid | 70 g |
| Distilled water | 930 g |
| | 1,000 g |

The arginine salt is dissolved in the distilled water and the solution is introduced into 1,000 cm³ solution bags under sterile conditions.

We claim:

1. Compounds derived from 3-hydroxybutanoic acid, characterized in that they are salts derived from an amino acid of natural origin, said amino acid containing at least two nitrogen groups per carboxyl group.

2. Compounds according to claim 1, characterized in that the aminoacid is L-arginine.

3. Compounds according to claim 1, characterized in that the aminoacid is L-lysine or L-histidine.

4. Compounds according to claim 1, characterized in that they are derived from the D(—) isomeric form of 3-hydroxybutanoic acid.

* * * * *